United States Patent [19]

Litke

[11] Patent Number: 4,477,607

[45] Date of Patent: Oct. 16, 1984

[54] THIXOTROPIC CYANOACRYLATE COMPOSITIONS

[75] Inventor: Alan E. Litke, Naugatuck, Conn.

[73] Assignee: Loctite Corporation, Newington, Conn.

[21] Appl. No.: 528,275

[22] Filed: Aug. 31, 1983

[51] Int. Cl.$^3$ .......................... C08K 9/04; C08K 5/54
[52] U.S. Cl. ................................. 523/212; 524/533; 524/850; 525/295
[58] Field of Search ............... 523/212; 524/533, 850; 525/295

[56] References Cited

U.S. PATENT DOCUMENTS

| | | | |
|---|---|---|---|
| 3,607,542 | 9/1971 | Leonard et al. | 524/555 |
| 3,663,501 | 5/1972 | Adams et al. | 523/212 |
| 3,839,065 | 10/1974 | Overhults et al. | 523/212 |
| 3,896,077 | 7/1975 | Leonard et al. | 524/425 |
| 3,940,362 | 2/1976 | Overhults | 523/212 |
| 4,076,685 | 2/1978 | Kogler | 523/139 |
| 4,102,945 | 7/1978 | Gleave | 525/315 |
| 4,180,911 | 1/1980 | Bullock | 106/35 |
| 4,180,913 | 1/1980 | Takeuchi et al. | 523/211 |
| 4,320,047 | 3/1982 | Murphy | 523/457 |

*Primary Examiner*—Herbert Lilling
*Attorney, Agent, or Firm*—Walter J. Steinkraus; Eugene F. Miller

[57] ABSTRACT

Cyanoacrylate compositions which employ fumed silicas treated with polydimethylsiloxane or trialkoxyalkylsilane are stable and exhibit an unexpectedly high thixotropic ratio. Such compositions are useful in adhesive applications or, when stabilized so as to prevent polymerization in contact with moisture, in latent fingerprint developing applications.

10 Claims, No Drawings

THIXOTROPIC CYANOACRYLATE COMPOSITIONS

BACKGROUND OF THE INVENTION

Cyanoacrylate adhesives based on esters of α-cyanoacrylic acid have gained wide acceptance in recent years for a broad range of industrial and consumer uses. The cyanoacrylate esters themselves, however, are very low viscosity liquids which makes the use of unfilled compositions difficult. Such compositions often migrate from the bondline or are absorbed into porous surfaces. Accordingly, there have been developed a variety of thickened cyanoacrylate adhesive compositions which incorporate organic polymers and/or inorganic fillers to reduce adhesive migration. Examples of such compositions are described in U.S. Pat. Nos. 3,607,542; 3,896,077, 4,105,715, 4,180,913 and in Chemical Abstracts 89:117907c; 89:216475u; 91:40425c; and 92:95114b.

In the art of thickened cyanoacrylates it is sometimes desirable that the composition display thixotropic properties. Thus, under high shear conditions the composition can be processed and easily applied to the substrate but once applied, will display significantly reduced migratory tendencies. It is also well known that the inclusion of fumed silicas in many organic liquid compositions produces thixotropic effects. The use of such silicas has been reported in cyanoacrylate compositions.

At least certain of the prior art cyanoacrylate compositions employing fumed silicas have displayed stability problems, however. Thus U.S. Pat. No. 3,607,542 describes organically filled cyanoacrylate compositions in which fumed silica is an optional ingredient. These compositions are reportedly stable for only up to 4 hours. Furthermore, the same patent states that silica by itself does not readily mix with cyanoacrylate monomer to form a paste.

Cyanoacrylate formulations also occasionally find non-adhesive applications. Thus, for instance, the vapors of methyl and ethyl cyanoacrylates have found use for developing latent fingerprints in law enforcement applications. For such applications it would be desirable to develop a nonflowable form of cyanoacrylate monomer so that small open containers of the monomer can be placed throughout a room or automobile to release vapors without the danger of accidental monomer spillage. Desirably the thixotropic additives will also be kept to a minimum so as not to substantially reduce the monomer vapor pressure.

In certain applications it has been discovered that hydrophobic silicas produced by treatment of fumed silica with dimethyldichlorosilane can be used to give thixotropic cyanoacrylate compositions with improved stability. However, these fillers add cure retarding strong acid to the cyanoacrylate composition. Also, the thixotropic ratio of these silicas in cyanoacrylate esters (the ratio of apparent viscosity is measured under specified high and low shear conditions) is quite low. Therefore, when very high thixotropic effects are desired, such as when a pasty composition is desired, the amount of acid introduced by the silica can substantially reduce the cure time of the composition. Also, for latent fingerprint developing type applications, higher silica levels may result in lower monomer vapor pressures.

Commercially available fumed silicas are also known which have been treated with hexamethyldisilazane. It has discovered that thixotropy ratios are also very low for these materials and that at least some of these materials tend to destabilize cyanoacrylate compositions. The destabilization effect is thought to result from residual ammonia or amine in the filler.

Accordingly there exists a need for a cyanoacrylate thixotrope, stable to the cyanoacrylate monomer, which has a significantly improved thixotropy ratio over dimethyldichlorosilane or hexamethyldisilazane treated silicas, and which does not adversely affect the fixture time of adhesive formulations.

SUMMARY OF THE INVENTION

The present application relates to cyanoacrylate compositions which employ fumed silicas treated with a polydimethylsiloxane or a trialkoxyalkylsilane as a thixotropic additive. It has been unexpectedly found that such silicas when incorporated into cyanoacrylate compositions do not adversely effect the stability of the composition, display a significantly higher thixotropy ratio than the previously mentioned treated silicas and, in adhesive compositions, do not adversely effect fixture time even at levels of about 10–12% where the compositions become pasty and very difficult to stir or apply uniformly.

The inventive compositions may consist primarily of an appropriately stabilized cyanoacrylate ester monomer and the specified silica. However, it is preferred that a small amount of an organic polymer such as polymethylmethacrylate be dissolved in the monomer.

The inventive compositions are also useful in nonadhesive applications such as nonflowable latent fingerprint developing formulations.

DETAILED DESCRIPTION OF THE INVENTION

Fumed silicas which have been found to impart desired thixotropic properties to the inventive compositions fall into two categories. The first, and most preferred, are polydimethylsiloxane treated silicas such as Cab-O-Sil N70-TS TM, sold by the Cabot Corporation. The silica has a carbon content of 5 weight percent and a surface area of $70M^2/gm$ according to the manufacturer.

The second category of silicas usable in the inventive compositions are trialkoxyalkylsilanes. An example is Aerosil R805 TM, an experimental product available from Degussa Corporation. Aerosil R805 TM is a trimethoxyoctylsilane treated silica having a surface area of 150 m²/gm.

The superior thixotropic performance of the inventive cyanoacrylate compositions is best obtained at silica levels of about 4–8%. These properties were demonstrated by comparative testing of an ethyl cyanoacrylate formulation containing 6% of a 0.4–0.5 million mw polymethylmethacrylate and 6% hydrophobic silica. The composition was stabilized with 5 ppm methanesulfonic acid (MSA) approximately 2500 ppm hydroquinone and 5 ppm $SO_2$. The formulations were prepared with the aforementioned Cab-O-Sil N70-TS TM and Aerosil R805 TM as well as two hexamethyldisilazane treated silicas (Tellenox 500 TM solb by Tulco, Inc. and Wacker HDK 2000 TM sold by Wacker-Chemie) and three-dimethyldichlorosilane treated silicas (Aerosils R972 TM, R974 TM and R976 TM, all sold by Degussa). Table I gives the results of comparative Brookfield viscosity and acid level (calculated as ppm MSA) determinations.

TABLE I

| Comp. | Silica | Brookfield Viscosity | | Ratio 2.5/20 | Total Acid |
|---|---|---|---|---|---|
| | | 2.5 RPM helipath (spindle) | 20 RPM helipath (spindle) | | |
| A | Cab-O-Sil N70-TS ™ | $2.9 \times 10^5$ (TE) | $4.2 \times 10^4$ (TE) | 6.9 | 27 |
| B | Aerosil R805 ™ | $1.4 \times 10^5$ (TE) | $2.8 \times 10^4$ (TE) | 5.0 | 32 |
| C | Tellenox 500 ™ | $4.4 \times 10^4$ (TE) | $2.1 \times 10^4$ (TE) | 2.1 | 26 |
| D | Wacker HDK2000 ™ | $3.3 \times 10^2$ (TA) | $3.0 \times 10^2$ (TA) | 1.1 | 29 |
| E | Aerosil R972 ™ | $1.2 \times 10^4$ (TC) | $3.8 \times 10^3$ (TC) | 3.2 | 38 |
| F | Aerosil R974 ™ | $2.1 \times 10^4$ (TC) | $5.2 \times 10^3$ (TC) | 4.0 | 40 |
| G | Aerosil R976 ™ | $2.6 \times 10^4$ (TC) | $8.1 \times 10^3$ (TC) | 3.2 | 39 |

As can be seen from the table, compositions A and B, which are within the invention, show much higher low shear viscosity and substantially higher thixotropic ratios than compositions C–G which are not within the invention. It was also observed that, when unagitated, compositions A and B were nonflowable gels whereas compositions C–G were all ungelled and pourable.

Compositions similar to formulation E but compounded with sufficient Aerosil R972 ™ to produce non-flowable gels comparable to those of compositions A and B in Table I have been prepared and have been observed to require longer fixture times than those of compositions A and B. This is believed to result from increased strong acid imparted by the dimethyldichlorosilane treated silica. The significantly higher acid numbers of compositions E–G is evidence that the dichlorosilane treated silicas do contribute strong acid to the cyanoacrylate formulations.

Both hexamethyldisilazine treated silicas had impractically low thixotropic ratios as shown by Table I. Furthermore, at least one of the hexamethyldisilazane treated silicas appars to destabilize cyanoacrylate monomers. Formulation C, which utilizes the Tellenox 500 ™ silica polymerized in less than one day in a sealed tube at 82° C. while compositions A, B and D–G all lasted at least 15 days under the same conditions.

It is preferred that the cyanoacrylate compositions of the invention include a minor amount of dissolved organic polymer. Suitable polymers include polyacrylates and polymethacrylates, polycyanoacrylates such as poly(ethyl cyanoacrylate), and poly(vinyl acetate) polymers and copolymers. The organic polymers are preferably included witin the range of approximately 1–15% of the composition by weight. Preferably, the organic polymers are included in the range of 3–10%. The inclusion of the organic polymer is recommended in order to prevent or significantly diminish the settling out of the silica from the inventive compositions. The compositions containing dissolved polymer are also observed to produce higher viscosities at equivalent silica concentrations and to recover thixotropic behavior faster after agitation than without dissolved polymers.

Other additives, conventional within the cyanoacrylate formulation art, may be included within the compositions of the invention without departing from the teaching hereof. Examples of such additives need not be specified since they are within the skill of those working in the art.

As mentioned above, it would be desirable for latent fingerprint developing applications to have a nonflowable form of cyanoacrylate with high vapor pressure. Gel compositions of the invention which have been stabilized to the point where they will not polymerize on contact with moisture are especially useful for such applications. The gel form pevents spillage and the over-stabilization guards against bonding of fingers ("finger-stick") are other articles. A typical such formulation includes 88% methylcyanoacrylate stabilized with 0.2% methane sulfonic acid and 2500 hydroquinone, 6% polymethylmethacrylate and 6% polydimethylsiloxane treated silica.

From the foregoing it can be seen that the invention is not limited by the specific examples set forth above, the invention being limited only as set forth in the following claims.

I claim:

1. In a composition comprising an α-cyanoacrylate ester monomer and a thixotropic agent, the improvement comprising that said composition is a non-flowable gel, said thixotropic agent is present in an amount of 12% or less and is a fumed silica having a surface treated with a trialkoxyalkylsilane and the said composition has a 2.5 RPM Brookfield viscosity of about $1 \times 10^5$ or greater.

2. A composition as in claim 1 wherein the silica surface is treated with trimethoxyoctylsilane.

3. A composition as in claim 1 comprising an organic polymer dissolved in said monomer.

4. A composition as in claim 3 wherein said polymer is selected from polyvinyl acetate polymers and copolymers, polyacrylates, polymethacrylates and polycyanoacrylates.

5. A composition as in claim 1 stabilized so as to be nonpolymerizable on contact with moisture.

6. A composition as in claim 3 wherein said polymer is present at levels of between 1 and 15% by weight.

7. A composition as in claim 6 wherein said polymer is present at levels of between 3 and 10% by weight.

8. A composition as in claim 7 wherein said polymer is polymethylmethacrylate.

9. A composition as in claim 1 wherein said silica is present in an amount between about 4 and 8% by weight.

10. A composition as in claim 9 wherein said silica is present in an amount of about 6% by weight.

* * * * *